United States Patent [19]

Chandraratna

[11] Patent Number: 5,006,550

[45] Date of Patent: Apr. 9, 1991

[54] CHROMAN ESTERS OF PHENOLS AND BENZOIC ACIDS HAVING RETINOID-LIKE ACTIVITY

[75] Inventor: Roshantha A. S. Chandraratna, El Toro, Calif.

[73] Assignee: Allergan, Inc., Irvine, Calif.

[21] Appl. No.: 458,883

[22] Filed: Dec. 29, 1989

[51] Int. Cl.$^5$ .................... A61K 31/35; C07D 311/04
[52] U.S. Cl. ........................... 514/456; 549/405
[58] Field of Search ..................... 549/405; 514/456

[56] References Cited

U.S. PATENT DOCUMENTS 4,739,098 4/1988 Chandraratna .................. 560/8
4,740,519 4/1988 Shroot et al. ................... 514/443

FOREIGN PATENT DOCUMENTS 130795 9/1985 European Pat. Off.
176034 4/1986 European Pat. Off.

OTHER PUBLICATIONS

Taguchi et al., C.A., 92:85928f (1980)–Abstract of Japan Kokai Tokkyo Koho 7995233 (7/27/79).
Sporn et al., in J. Amer. Acad. Derm., 15:756–764 (1986).
Shudo et al., in Chem. Phar. Bull., 33:404–407 (1985).
Kagechika et al., in J. Med. Chem., 31:2182–2192 (1988).

Primary Examiner—Nicky Chan
Attorney, Agent, or Firm—Gabor L. Szekeres; Martin A. Voet; Robert J. Baran

[57] ABSTRACT

Retinoid like activity is exhibited by compounds of the formula

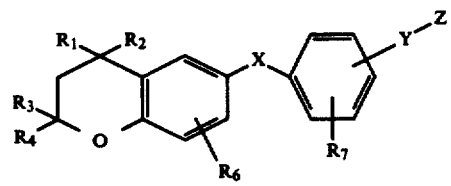

wherein the $R_1$–$R_7$ groups are independently H or straight chain or branched chain lower alkyl or cycloalkyl of 1 to 6 carbons; X symbolizes an ester or thioester linkage, Y is cycloalkyl or branched chain alkyl of 1 to 6 carbons or is ($CH_2$) where n is an integer between 0 to 6 or is an alkenyl group of 2 to 6 carbons, or an alkynyl group of 2 to 6 carbons; and Z is H, OH, OR', OCOR', —COOH or a pharmaceutically acceptable salt, ester or amide thereof, —$CH_2OH$ or an ether or ester derivative, or —CHO or an acetal derivative, or —COR' or a ketal derivative where R' is an alkyl, cycloalkyl or alkenyl group containing 1 to 6 carbons, or a phenylalkyl, phenyl or substituted phenyl group.

28 Claims, No Drawings

CHROMAN ESTERS OF PHENOLS AND BENZOIC ACIDS HAVING RETINOID-LIKE ACTIVITY

BACKGROUND

This invention relates to novel compounds having retinoid-like activity. More specifically, the invention relates to compounds having a substituted chroman portion and a substituted phenyl portion linked to the 6-position of the chroman nucleus through an ester or thioester group.

RELATED ART

Carboxylic acid derivatives useful for inhibiting the degeneration of cartilage of the general formula 4-(2-(4,4-dimethyl-6-X)-2-methylvinyl)benzoic acid where X is tetrahydroquinolinyl, chromanyl or thiochromanyl are disclosed in European Patent Application 0133795 published Jan. 9, 1985. European Patent Application 176034A published Apr. 2, 1986 discloses tetrahydronaphthalene compounds having an ethynylbenzoic acid group. U.S. Pat. No. 4,739,098 discloses compounds of retinoid-like activity where three olefinic units from the acid-containing moiety of retinoic acid are replaced by an ethynylphenyl functionality.

The publication by Sporn et. al. in *J. Amer. Acad. Derm.* 15:756–764 (1986) discloses the compound 4-(5,5,8,8-tetramethyl5,6,7,8-tetrahydro-2-naphthoylamino) benzoic acid as a retinoid-like agent. Further compounds of background interest to the present invention are disclosed by Shudo et al. in *Chem. Phar. Bull.* 33:404–407 (1985); and by Kagechika et. al. in *J. Med. Chem.* 31: 2182–2192 (1988).

SUMMARY OF THE INVENTION

This invention covers compounds of Formula 1

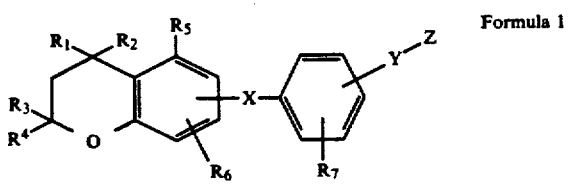

Formula 1 wherein the $R_1$–$R_7$ groups are independently H or straight chain or branched chain lower alkyl or cycloalkyl of 1 to 6 carbons; X symbolizes an ester or thioester linkage, Y is cycloalkyl or branched chain alkyl of 1 to 6 carbons or is $(CH_2)_n$ where n is an integer between 0 to 6 or is an alkenyl group of 2 to 6 carbons, or an alkynyl group of 2 to 6 carbons; and Z is H, OH, OR', OCOR', —COOH or a pharmaceutically acceptable salt, ester or amide thereof, —CH$_2$OH or an ether or ester derivative, or —CHO or an acetal derivative, or —COR' or a ketal derivative where R' is alkyl, cycloalkyl or alkenyl group containing 1 to 6 carbons, a phenylalkyl, phenyl or substituted phenyl group.

A second aspect, this invention relates to the use of the compounds of Formula 1 for treating dermatoses, such as acne, Darier's disease, psoriasis, icthyosis, eczema, atopic dermatitis and epithelial cancers. These compounds are also useful in the treatment of arthritic diseases and other immunological disorders (e.g. lupus erythematosus), in promoting wound healing, in treating dry eye syndrome and in reversing the effects of sun damage to skin.

This invention also relates to a pharmaceutical formulation comprising a compound of Formula 1 in admixture with a pharmaceutically acceptable excipient.

In another aspect, this invention relates to the process for making a compound of Formula 1 which process comprises reacting compounds of Formula 2 with compounds of Formula 3,

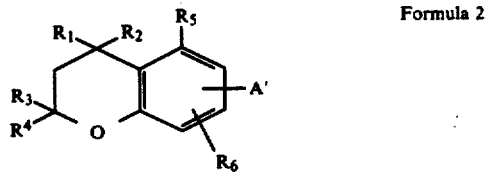

Formula 2

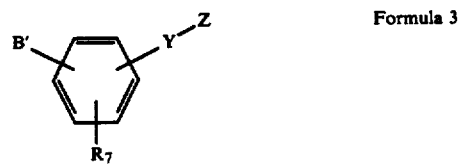

Formula 3 where $R_1$–$R_7$, Y and Z are defined as above in connection with Formula 1, and wherein one of A' and B' is an OH or SH group, and the other is a carboxylic acid (COOH) or an appropriate derivative (such as an acid chloride) suitable for forming an ester with a hydroxyl or thiol group, and where the reaction is conducted under conditions suitable for forming an ester or thioester bond between the chroman ring of the compound of Formula 2 and the phenyl ring of the compound of Formula 3.

In the process of reacting compounds of Formula 2 with the compounds of Formula 3 to form the ester or thioester linkage X of Formula 1, when Z is an alcohol or acid function it is preferred that such alcohol or acid function be protected. When, in the esterification reaction Z is an aldehyde or ketone, it may not need to be protected depending on the precise nature of the compounds and the conditions of the esterification reaction.

In still another aspect, the present invention also relates to preparation of compounds of Formula 1 by Conversion compounds having the structure of Formula 4.

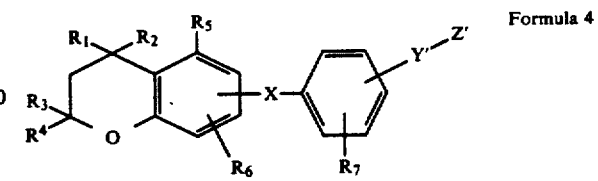

Formula 4

In Formula 4 the symbols $R_1$–$R_7$ and X are defined as above in connection with Formula 1, and Y'–Z' symbolizes such precursors of the groups Y–Z which can be readily converted by reactions well known to organic chemists, into the desired groups Y–Z. Thus, the present invention also relates to the above-noted processes involvings steps such as:

converting an acid of Formula 4 to a salt; or
forming an acid addition salt;
converting an acid of Formula 4 to an ester; or
converting an acid or ester of Formula 4 to an amide; or
reducing an acid or ester of Formula 4 to an alcohol or aldehyde; or converting an alcohol of Formula 4 to an ether or ester; or oxidizing an alcohol of Formula 4 to an aldehyde; or converting an aldehyde of Formula 4 to an acetal; or converting a ketone of Formula 4 to a ketal, extending by homologation the length of the alkyl chain of a compound of Formula 4, where Y' is alkyl.

GENERAL EMBODIMENTS

Definitions

The term "ester" as used here refers to and covers any compound falling within the definition of that term as classically used in organic chemistry. The term "thioester" as used here refers to and covers any compound falling within the definition of that term as classically used in organic chemistry. With respect to the ester or thioester function symbolized by X in Formula 1 linking the chroman and phenyl moieties of the compounds of the invention, the function includes an ester or thioester derived from a phenol or thiophenol and a 6-chromanoic acid derivative (when the carbonyl group is directly attached to the chroman nucleus) and also an ester or thioester derived from a benzoic acid and 6-hydroxy-chroman or 6-thiohydroxy-chroman derivative (when the carbonyl group is directly attached to the phenyl nucleus).

Where Z (of Formula 1) is —COOH, the term "ester" covers the products derived from treatment of this function with alcohols. Where the ester is derived from compounds where Z is —CH$_2$OH, this term covers compounds of the formula —CH$_2$OOCR where R is any substituted or unsubstituted aliphatic, aromatic or aliphatic-aromatic group.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids or alcohols. Here, and where ever else used, lower alkyl means having 1–6 carbon atoms and includes straight as well as branched chain alkyl groups. Also preferred are the phenyl or lower alkylphenyl esters.

Amide has the meaning classically accorded that term in organic chemistry. In this instance it includes the unsubstituted amides and all aliphatic and aromatic mono-and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly amides are those derived from lower alkyl amines. Also preferred are mono- and di-substituted amides derived from the phenyl or lower alkylphenyl amines. Unsubstituted amides are also preferred.

Acetals and ketals include the radicals of the formula —CK where K is (—OR)$_2$. Here, R is lower alkyl. Also, K may be —OR$_1$O— where R$_1$ is lower alkyl of 2–5 carbon atoms, straight chain or branched.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating such as methyl iodide. Preferred salts are those formed with inorganic acids such as hydrochloric acid, sulfuric acid or phosphoric acid. Any of a number of simple organic acids such as mono-, di- or tri-acid may also be used.

The preferred compounds of this invention are those where the X functionality of Formula 1 is COO— with the carbonyl group attached to the 6-position of the chroman nucleus. In other words, preferred compounds of the invention are phenyl ester derivatives of 6-carboxy chromans.

Within the above-noted preference, still more preferred are compounds where in the Y-Z functionality of Formula 1 n is zero and Z is either COOH or COOR" (R" being lower alkyl, lower cycloalkyl, phenyl substituted lower alkyl, phenyl or substituted phenyl). In other words, still more preferred are esters of 6-carboxy chromans formed with hydroxy benzoic acids, or with hydroxy benzoic acid esters. Within this group, esters of substituted 6-carboxy chromans with 4-hydroxy benzoic acid and particularly with 4-hydroxy benzoic acid esters are still more preferred.

Even more preferred are compounds which, in addition to having the hydroxy-benzoic acid or hydroxy-benzoic acid ester residue, include substituents in the 2,2 and/or in the 4,4 and/or in the 7 position of the 6-chromanoic acid moiety. Within this group derivatives of 2,2,4,4-tetramethyl and 2,2,4,4,7 pentamethyl 6-chromanoic acid are most preferred.

The most preferred specific compounds of the invention are shown in Formula 5, and are identified as follows:

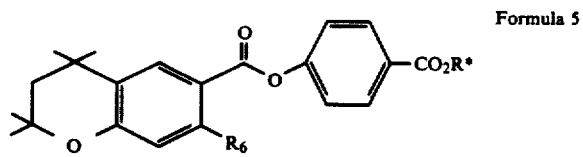

Formula 5

Ethyl 4-(2,2,4,4-tetramethyl-6-chromanoyloxy) benzoate (Compound 1, R$_6$=H and R*=ethyl);

4-(2,2,4,4-tetramethyl-6-Chromanoyloxy) benzoic acid (Compound 2, R$_6$=H and R*=H);

Ethyl 4-(2,2,4,4,7-pentamethyl-6-chromanoyloxy) benzoate (Compound 3, R$_6$=methyl and R*=ethyl), and 4-(2,2,4,4,7-pentamethyl-6-chromanoyloxy) benzoic acid (Compound 4, R$_6$=methyl and R*=H)

The compounds of this invention may be administered systemically or topically, depending on such considerations as the condition to be treated, need for site-specific treatment, quantity of drug to be administered, and similar considerations.

In the treatment of dermatoses, it will generally be preferred to administer the drug topically, though in certain cases such as treatment of severe cystic acne, oral administration may also be used. Any common topical formulation such as a solution, suspension, gel, ointment, or salve and the like may be used. Preparation of such topical formulations are well described in the art of pharmaceutical formulations as exemplified, for example, *Remington's Pharmaceutical Science*, Edition 17, Mack Publishing Company, Easton, PA. For topical application, these compounds could also be administered as a powder or spray, particularly in aerosol form.

If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or intermuscular injection.

Other medicaments can be added to such topical formulation for such secondary purposes as treating skin dryness, providing protection against light; other medications for treating dermatoses, preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of, for example, acne, or other such dermatoses, that a formulation containing between 0.001 and 5 percent by weight, preferably about 0.01 to 1% will usually constitute a therapeutically effective concentration. If administered systemically, an amount between 0.01 and 100 mg per kg body weight per day, but preferably about 0.1 to 10 mg/kg, will effect a therapeutic result in most instances.

The retinoic acid like activity of these compounds was confirmed through the classic measure of retinoic acid activity involving the effects of retinoic acid on ornithine decarboxylase. The original work on the correlation between retinoic acid and decrease in cell proliferation was done by Verma & Boutwell, *Cancer Research*, 1977, 37, 2196-2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increase are unknown, it is known that 12-0-tetradecanoyl-phorbol-13-acetate (TPA) induces ODC activity. Retinoic acid inhibits this induction of ODC activity by TPA. The compounds of this invention also inhibit TPA induction of ODC as demonstrated by an assay essentially following the procedure set out in *Cancer Res.*, 35: 1662-1670, 1975.

By way of example of retinoic acid-like activity it is noted that in the assay conducted essentially in accordance with the method of Verma & Boutwell, ibid, the following examples of the preferred compounds of the present invention (Compounds 1, 2 and 3) attained an 80% inhibition of TPA induced ODC activity at the following concentrations ($IC_{80}$):

| Compound | $IC_{80}$ conc (nmols) |
|---|---|
| 1 | 41 |
| 2 | 165 |
| 3 | 3.0 |

Specific Embodiments

The compounds of this invention can be made by a number of different synthetic chemical pathways. To illustrate this invention, there is here outlined a series of steps which have been proven to provide the compounds of Formula 1 when such synthesis followed is in fact and in spirit. The synthetic chemist will readily appreciate that the conditions set out here are specific embodiments which can be generalized to any and all of the compounds represented by Formula 1. Furthermore, the synthetic chemist will readily appreciate that the herein described synthetic steps may be varied and or adjusted by those skilled in the art without departing from the scope and spirit of the invention.

The compounds of the invention, in accordance with Formula 1 are esters or thioesters containing a chroman moiety and a phenyl moiety. Accordingly, and speaking generally, the compounds of the invention can be made from the appropriate carboxylic acid or derivatized carboxylic acid precursors on the one hand and thiol or alcohol precursors on the other, by synthetic methods which per se are known in the art.

Specifically, the compounds of the invention (shown in Formula 1) can be made by reaction of the precursors shown in Formula 2 and Formula 3. As is noted above, in these formulas either A' or B' is an OH or an SH group, and the other is a carboxylic acid (COOH) or a derivatized carboxylic acid (such as an acid chloride) which is capable of forming an ester or a thioester with the other group.

More specifically, and by way of example, preferred compounds of the invention comprise esters of substituted 6-carboxy chromans i.e. esters derived from compounds of Formula 2 where A' is COOH) with hydroxybenzoic acid esters (compounds of Formula 3 where n of Y is zero and Z is COOR*, R* being an esterifying alkyl, alkylphenyl or phenyl group). These compounds can be prepared in accordance with Reaction Scheme 1. In this reaction the free acid, a 6-carboxychroman derivative (compound of Formula 2), is reacted with the hydroxybenzoic acid ester (compound of Formula 3) in a suitable solvent such as methylene chloride ($CH_2Cl_2$) in the presence of dicyclohexyl carbodiimide (DCC) and dimethylaminopyridine (DMAP). In Reaction Scheme 1 the symbols $R_1$ through $R_7$ have the same definition as in Formula 1.

Reaction Scheme 1

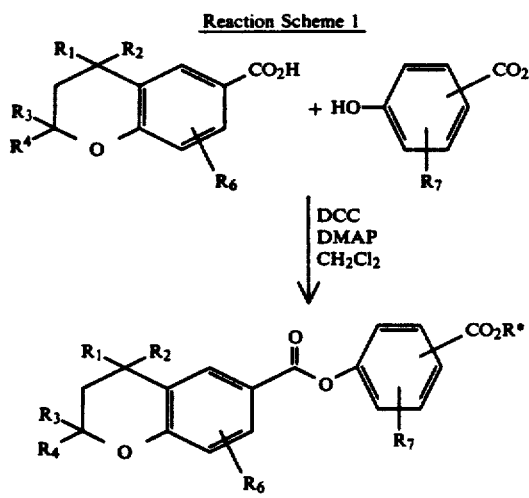

Reaction Scheme 2 shows an alternative process for synthesizing the compounds which are obtainable in Reaction Scheme 1. In accordance with this process, the substituted 6-carboxychroman derivatives are first converted to the corresponding acid chloride by treatment with a suitable reagent, for example, thionyl chloride ($SOCl_2$). The corresponding acid chloride is thereafter reacted with a hydroxybenzoic acid ester in a suitable solvent and preferably in the presence of an acid acceptor, such as triethylamine.

Reaction Scheme 2

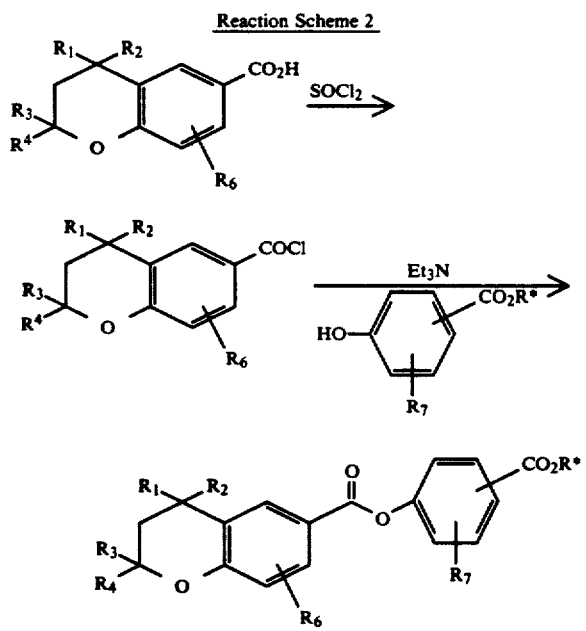

Reaction Scheme 3 shows a process for making esters of substituted 6-carboxychromans with hydroxy benzoic acid derivatives, where the desired products, (compounds of the invention) have a free carboxylic acid group. This process is similar to the condensation, in the presence of DCC and DMAP, shown in Reaction Scheme 1, except that a benzyl ester of the hydroxybenzoic acid is employed, and that in the last step of the process the benzyl ester function is selectively cleaved by hydrogenation over palladium (or other suitable catalyst), to provide the target compound having a free carboxylic acid group attached to the phenyl moiety.

REACTION SCHEME 3

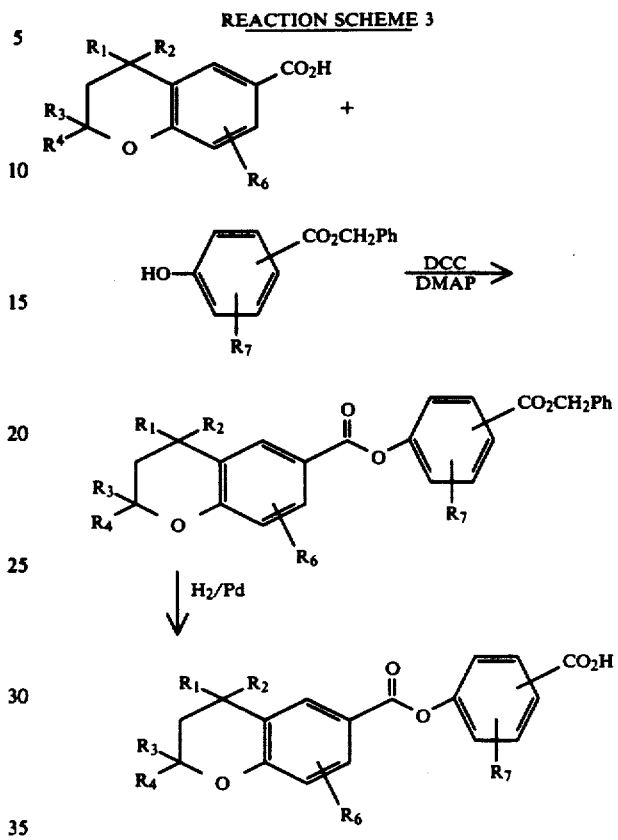

Reaction Scheme 4 shows an exemplary process for the preparation of compounds of the invention derived from substituted 6-hydroxy chromans and terephathalic acid half esters, that is, compounds where, with reference to Formula 1, X is COO with the carbonyl group attached to the phenyl moiety, and n of Y is zero. The condensation shown in this reaction is performed in the presence of DCC and DMAP. It should be understood however, that several variations of this process are possible, for example the terephathalic acid half ester can be converted into an acid chloride (or some other activated derivative of the carboxylic acid) and the acid chloride (or other active derivative) can be reacted with the 6-hydroxy-chroman derivative in a suitable solvent and in the presence of an acid acceptor, in analogy to the reaction sequence shown in Reaction Scheme 2. Utilizing the benzyl half ester of terephatalic acid (or of a substituted terephtalic acid) in analogy with Reaction Scheme 3, permits selective cleavage of the benzyl ester function by hydrogenation, and synthesis of the corresponding 6-hydroxy-chroman derivative esterified with terephatalic acid and bearing, attached to the phenyl, group a free carboxylic acid function.

Reaction Scheme 4

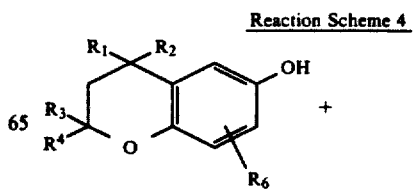

-continued
Reaction Scheme 4

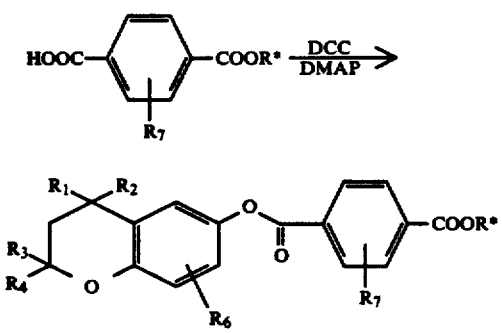

The synthetic procedures outlined in an exemplary manner in connection with Reaction Schemes 1–4, can also be adapted for the preparation of the thioester compounds of the present invention.

As is noted above in connection with Formula 4, compounds of the invention (Formula 1) may also be prepared by performing certain synthetic steps on compounds which are either already embraced by Formula 1, or are such precursors shown in Formula 4, which readily lend themselves to synthetic steps leading to compounds of the invention. In this regard free carboxylic acids of Formula 4, that is compounds possessing the "chroman to phenyl" ester linkage but having a free or appropriately protected carboxylic group on the phenyl moiety, can be converted to salts, esterified, converted to an amide, reduced to an dehyde or an alcohol. The corresponding alcohols and aldehydes can be esterified or converted to acetals, as applicable. Alternatively the carbon chain of Y–Z of Formula 1 may be subjected to chain elongation by homologation. As it will be recognized by those skilled in synthetic organic chemistry, the foregoing conversions can be performed by adapting generally known synthetic procedures to the compounds of the invention. In performing some of the above-noted synthetic steps on compounds of Formula 1 or of Formula 4, care may need to be exercised not to saponify or otherwise destroy the ester linkage between the chroman and phenyl moieties.

The compounds of Formula 3 which comprise starting materials or intermediates to the compounds of the present invention, are either available commercially, or are readily synthesized by known synthetic methods within the skill of ordinary artisan in the field. For example, 4-hydroxy benzoic acid is commercially available, and can be esterified to provide, for example, ethyl 4-hydroxy benzoate which is an important intermediate for the synthesis of certain specific examples of the compounds of the present invention. The mono ethyl ester of terephatalic acid, another intermediate in accordance with Formula 3, is also available commercially or is readily synthesized by known methods.

Intermediates of Formula 2 where A' is COOH, can be synthesized by the reaction sequences described below.

Specifically, compounds of Formula 2 where $R_3$–$R_6$ are hydrogen, and A' is COOH are synthesized according to Reaction Scheme 5.

Reaction Scheme 5

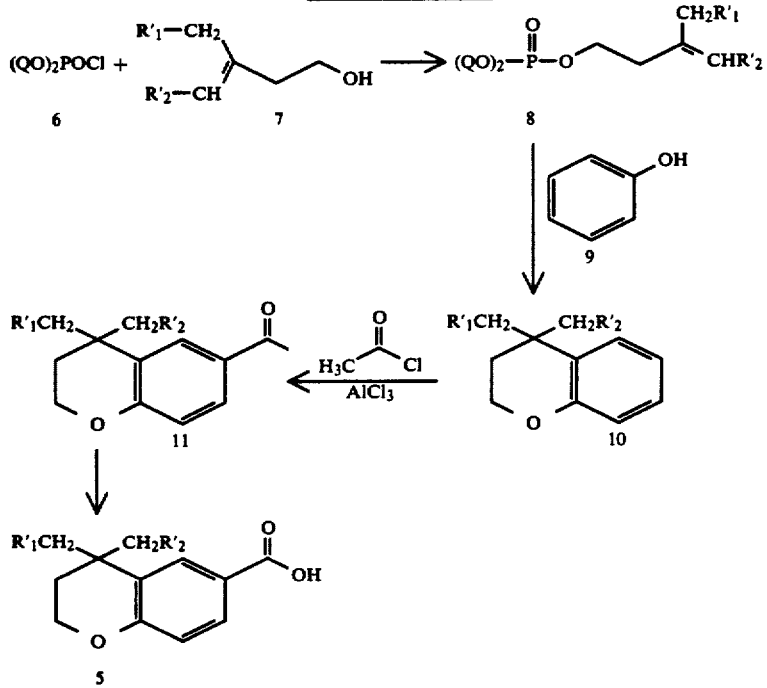

In Reaction Scheme 5 Q is phenyl and $R_1'$ and $R_2''$ are hydrogen or lower alkyl having 1 to 5 carbons. The reaction sequence is hereinafter further described generally but with emphasis to the preferred case where $R_1'$ and $R_2''$ both are hydrogen, i.e. for the synthesis of 4,4-dimethyl-6-carboxy chroman (Compound 5).

With reference to Reaction Scheme 5, the phosphate (Compound 8) is prepared from the corresponding diphenyl chlorophosphate (Compound 6) and 3-methyl-3-butene-1-ol (Compound 7, $R_1'$ and $R_2''$ are both H) available from Aldrich, or prepared by means known in the art. It is preferred to prepare Compound 8 by dissolving the alcohol 7 in about a 10% excess of pyridine or the like under an inert atmosphere cooled to approximately −10 degrees to 10 degrees C. This solution is then added drop-wise, under an inert atmosphere, to a solution of diphenyl chlorophosphate 6, in about an equal amount of the reaction solvent. About a 2-5% molar excess of diphenyl chlorophosphate 6 relative to the alcohol 7 is employed. The atmosphere may be argon, nitrogen, or another inert gas. The mixture is heated at reflux for between 1 and 5 hours, preferably about 3, to effect the reaction. The product is then recovered by conventional means. The diphenyl phosphate ester (Compound 8) is then reacted with phenol 9 to effect formation of chroman (Compound 10). For example, phenol 9 is added to a flask already containing stannic chloride under argon which has been cooled to between −10 degrees to 10 degrees C. After thorough mixing of this combination for about 15 minutes to an hour at the reduced temperature, the phosphate 8 is added at the reduced temperature. Both of these steps are carried out under an inert atmosphere such as argon or nitrogen. When the addition of the phosphate 8 is completed, the mixture is stirred at about ambient temperature for up to 24 hours. Then the reaction is quenched with a dilute solution of aqueous alkali metal base or the like. The product is recovered by extraction and other conventional means.

The carboxylic acid function is introduced into the 6-position of the 4,4-disubstituted chroman (Compound 10) by acetylation with acetyl chloride in the presence of a Friedel Crafts type catalyst, such as AlCl$_3$. Thereafter, the acetyl group of the resulting 4,4-dialkyl-6-acetyl-chroman (Compound 11 is oxidized to a carboxyl group with an oxidizing agent such as sodium hypochlorite (NaOCl) and the intermediate 4,4-dialkyl-6-carboxy chroman, when $R_1'$ and $R_2'$ are both H, 4,4-dimethyl 6-carboxy chroman (Compound 5)) is obtained.

Compounds of Formula 2 where $R_3$-$R_5$ are hydrogen, $R_6$ is lower alkyl, and A' is COOH, are synthesized according to Reaction Scheme 6. This scheme will serve as an illustrative example for the synthesis of compounds of the invention having substituents in the 4,4 and 7 positions of the chroman nucleus. In this scheme 4,4-dimethyl-6-carboxychroman 5 (or its derivatives, when $R_1'$ and $R_2'$ are lower alkyl of 1 to 5 carbons) serve as starting materials. Thus, Compound 5, obtainable in accordance with Reaction Scheme 5, is converted to the corresponding acid chloride and thereafter to the corresponding diethylamide (Compound 12) through treatment with thionyl chloride and subsequently by treatment with diethylamine. The lower alkyl substituent at the 7 position of the chroman nucleus of Compound 12 is introduced by alkylation with an alkyl halide ($R_6$-X), after treating 12 with secondary butyl lithium in tetramethylethylenediamine (TMEDA). The resulting 7-substituted diethylamide (Compound 13) is thereafter converted into the corresponding 4,4,7 substituted 6-carboxy chroman 14 for example by heating with approximately 10% aqueous sodium hydroxide solution or 10 percent perchloric acid solution.

REACTION SCHEME 6

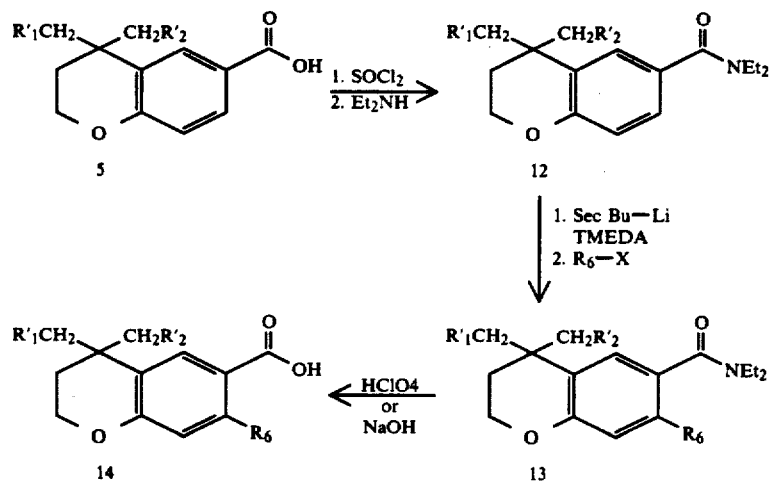

The intermediate chroman derivatives of Formula 2 where $R_1$-$R_4$ all are lower alkyl, $R_5$ is H or lower alkyl, $R_6$ is H or lower alkyl, and A' is COOH, may be prepared in accordance with the synthetic steps illustrated in Reaction Scheme 7.

REACTION SCHEME 7

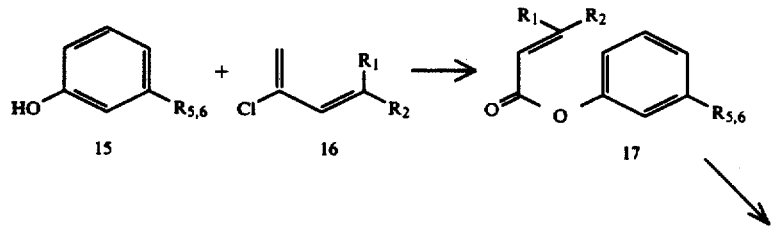

-continued
REACTION SCHEME 7

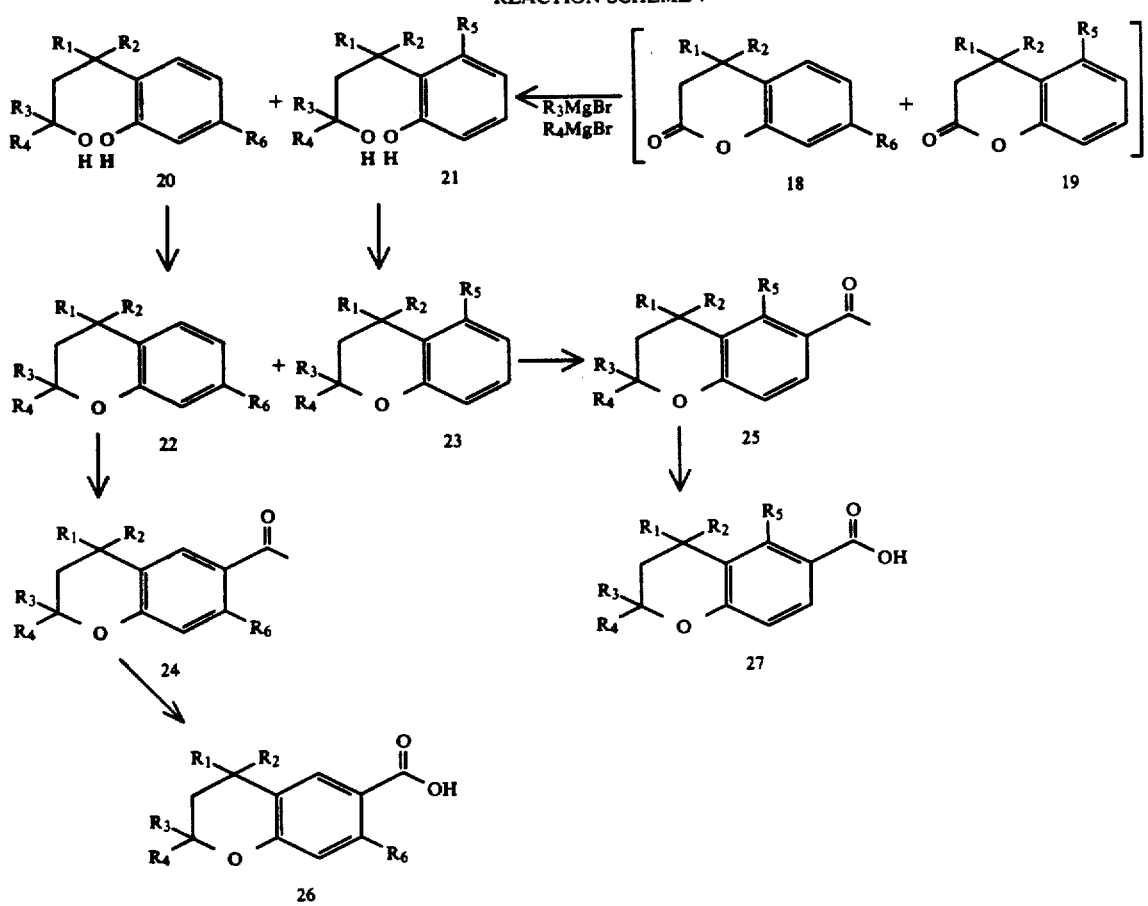

Thus, in accordance with Reaction Scheme 7, phenol, or a phenol substituted in the 3 (meta) position by an alkyl substituent (Compound 15) is acylated with an acylating agent, such as the acid chloride (Compound 16) derived from 3,3-dimethyl acrylic acid or from another appropriately substituted acrylic acid. As is described below, due to formation of positional isomers the alkyl substituent in the 3 (meta) position of the phenol compound 15 becomes, in the target compounds of Formulas 1 and 2, either the $R_5$ substituent or the $R_6$ substituent. (Designation of this meta substituent in Reaction Scheme 7 as "$R_{5,6}$" is indicative of this fact). When the acid chloride 16 is derived from acrylic acid (and not from another substituted acrylic acid derivative) then the reaction sequence gives rise to compounds of Formula 2 where $R_3$ and $R_4$ are lower alkyl and $R_1$ and $R_2$ are hydrogen. That reaction sequence is specifically illustrated in Reaction Scheme 8.

Thus, with specific reference to R ⓡaction Scheme 7 the acylation of phenol Compound 15 with the acid chloride 16 is preferably conducted in the presence of a strong base (e.g. sodium hydride) in an inert solvent (such as tetrahydrofuran). The resulting substituted phenyl-acrylate is Compound 17.

The substituted phenyl-acrylate 17 is ring closed under Friedel Crafts type reaction conditions ($AlCl_3$ catalyst, in an inert solvent such as methylene chloride) to provide two positional isomers Compound 18 and Compound 19 of the 2-oxo-chroman derivative, each of which bears, in the 4-position, the $R_1$ and $R_2$ substituents. Compound 18 has the alkyl substituent (derived from the meta position of phenol compound 15) in the 7-position of the chroman moiety, whereas Compound 19 has the same substituent in the 5-position of the chroman nucleus. The 2-oxo-chromans 18 and 19 are thereafter treated with a Grigna reagent to introduce the $R_3$ and $R_4$ substituents. In the preferred embodiments $R_3$ and $R_4$ are identical, for example both are methyl or ethyl. When $R_3$ and $R_4$ are methyl, the Grignard reagent is preferably methylmagnesium chloride (dissolved in tetrahydrofuran). A solution of compound 18 or of Compound 19, (or of a mixture of the two isomers) in a suitable solvent, for example in dry diethylether, is added to this Grignard reagent. The resulting phenols containing a tertiary alcohol side chain, (that is molecules in which the chroman ring had been opened) are shown in Reaction Scheme 7 as Compound 20 and Compound 21.

Compound 20 and Compound 21 which already have the desired $R_1$, $R_2$, $R_3$, and $R_4$ substituents, are ring closed under acidic conditions, (e.g. by heating in aqueous sulfuric acid) to provide the chroman derivatives (Compound 22 and Compound 23). Compound 22 and Compound 23 are then acetylated under Friedel Crafts type conditions with acetyl chloride to provide the 6-acetyl chroman derivatives Compounds 24 and Compound 25. Compounds 24 and Compound 25 are then oxidized, for example with aqueous sodium hypochlorite (NaOCl), to provide the desired 6-Carboxychroman compounds 26 and 27.

Reaction Scheme 8

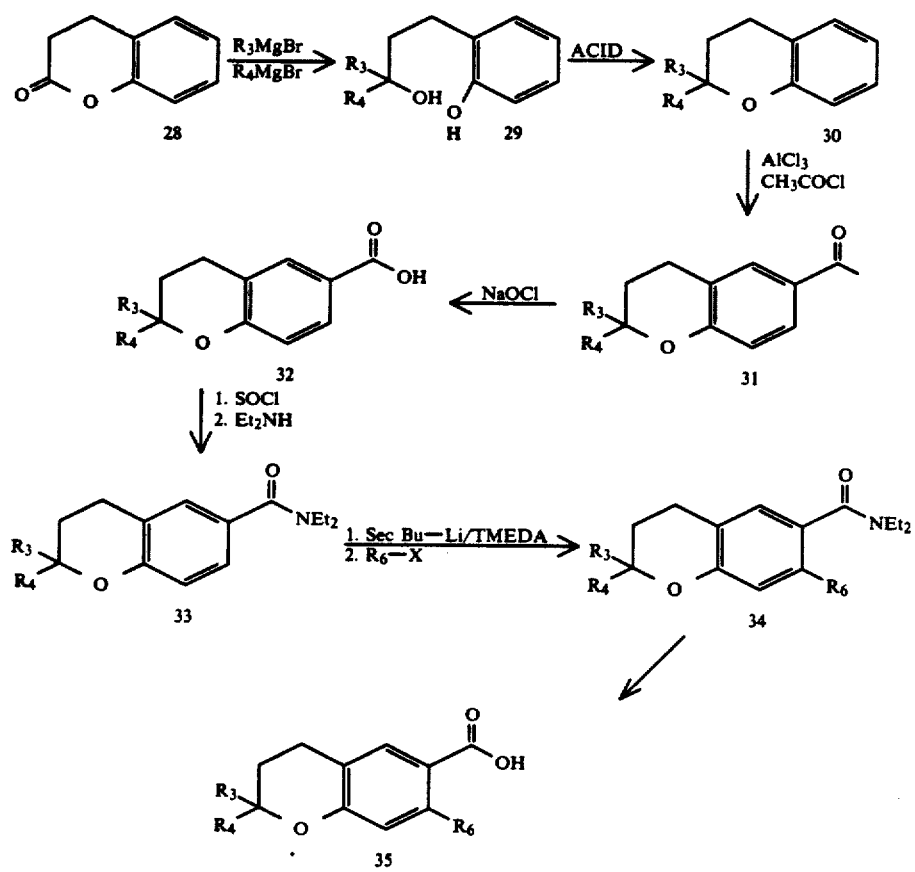

The synthetic sequence which provides 6-carboxychroman intermediates unsubstituted in the 4 and 5 positions, and substituted or unsubstituted in the 7-position, is shown in Reaction Scheme 8. The unsubstituted 2-oxo-chroman (dihydrocoumarin, Compound 28) shown in Reaction Scheme 8 can be obtained, for example, by the steps outlined in Reaction Scheme 7 using acrylic acid chloride ($R_1$, $R_2$=H in Compound 16) and phenol ($R_5$, $R_6$=H in Compound 15). Dihydrocoumarin (Compound 28) is subjected to the reaction sequence outlined in Reaction Scheme 8 to yield, through the intermediate compounds 29, 30 and 31, the 2,2 disubstituted 6-carboxychromans (Compound 32). Compound 32 then can be reacted with an appropriate compound of Formula 3 to provide the esters of the invention, in accordance with Formula 1.

Alternatively, the 2,2 disubstituted 6-carboxychroman (Compound 32) may be alkylated in the 7-position of the chroman nucleus in accordance with the synthetic sequence described above in Reaction Scheme 6 in connection with the analogous alkylation of 4,4 disubstituted 6-carboxychromans 5. Thus, with specific reference now to Reaction Scheme 8, Compound 32 is first converted to the corresponding acid chloride and then to the corresponding diethylamide (Compound 33). The diethylamide 33 is alkylated in the presence of secondary buthyl lithium in tetramethylethylene diamine. The resulting 7-substituted diethylamide (Compound 34) is thereafter converted into the corresponding 2,2,7 substituted 6-carboxychroman 35 for example by hydrolysis with aqueous base or acid.

The following examples of specific compounds of the invention, and specific examples of the synthetic steps in which the compounds and certain intermediates are made, are set out to illustrate the invention, not to limit its scope.

SPECIFIC EXAMPLES

Diphenyl-3-methyl-3-buten-1-yl phosphate (Compound 36)

To an ice-cooled solution of 12.2 g (141.65 mmol) of 3-methyl-3-buten-1-ol (Compound 7) (Aldrich) and 11.9 g (150.44 mmol) of pyridine in 100 ml of tetrahydrofuran was added dropwise under argon a solution of 38.5 g (143.21 mmol) of diphenyl chlorophosphate (Compound 6) in 100ml of tetrahydrofuran. The mixture was heated at reflux for 3 hours and then cooled and filtered. The filtrate was concentrated in vacuo and the residue dissolved in 400 ml of 1:1 ether and hexane and then washed with 2×200 ml water, 75 ml saturated NaCl solution and dried (MgSO$_4$). The solvent was removed in vacuo to give the title compound as a pale yellow oil. PMR (CDCl$_3$): & 1.69 (3H, s), 2.37 (2H, t, J~7 Hz), 4.32 (2H, q, J~7 Hz), 4.72 (1H, s), 4.80 (1H), 7.10–7.35 (10H, m).

4,4-Dimethylchroman (Compound 37)

To a dry, ice-cooled flask containing 34.95g (0.134 mol) of stannic chloride was added quickly under argon 63.0g (0.669 mol) of phenol. The mixture was stirred at 0 degrees C for 0.5 hour and then treated with 43.0g (0.135 mol) of diphenyl-3-methyl-3-buten-1-yl phosphate (Compound 36), followed by a 5 ml carbon disulfide rinse. The mixture was stirred at room temperature for 21 hours and then quenched by pouring onto 700 g ice and 1 liter of 1.5N NaOH. The mixture was extracted with 1×600 ml and 2×300 ml ether. The combined ether fractions were washed with 2N NaOH, saturated NaCl and dried (MgSO$_4$). Solvent was removed in vacuo and the residue purified by flash chromatography (silica; 2% ether in hexane) to give the title compound as a colorless oil. PMR (CDCl$_3$) &: 1.34 (6H), 1.80–1.85 (2H, m), 4.15–4.20 (2H, m), 6.80 (1H, dd, J~8.1 hz, 1.5 Hz), 6.87 (1H, td, J~8.1 Hz, 1.5 Hz), 7.07 (1H, td, J~8.1 Hz, 1.5 Hz), 7.26 (1H, dd, J~8.1 Hz, 1.5 H).

In a similar manner, but substituting the corresponding 3 alkylphenol for phenol, there may be prepared the following compounds:
4,4,7-trimethylchroman;
4,4-dimethyl-7-ethylchroman;
4,4-dimethyl-7-propylchroman; and
4,4-dimethyl-7-pentylchroman.

4,4-Dimethyl-6-acetylchroman (Compound 38)

To a stirred solution of 7.94g (48.9425 mmol) of 4,4-dimethylchroman (Compound 37) in 70 ml of nitromethane was added under argon 4.0 g (50.96 mmol) of acetyl chloride followed by 6.8 g (51 mmol) of aluminum chloride. This was stirred at room temperature for 5.5 hours and then cooled in an ice bath and treated slowly with 70 ml of 6N hydrogen chloride. The resultant mixture was stirred at room temperature for 10 minutes and then treated with 100 ml ether and the organic layer separated. The organic layer was washed with water saturated NaHCO$_3$ and saturated NaCl solutions and dried (MgSO$_4$). Solvent was removed in vacuo and the residue purified by flash chromatography (silica; 10% ethyl acetate in hexanes). This was followed by kugelrohr distillation (95–100 degrees C.; 0.15 mm) to give the title compound as a colorless oil. PMR (CDCl$_3$): & 1.40 (6H), 1.95–2.00 (2H, m), 2.58 (3H), 4.25–4.30 (2H, m), 6.83 (1H, d, J~8.0 Hz), 7.62 (1H, dd, J~8.0 Hz, 1.5 Hz), 8.00 (1H, d, J~1.5 Hz).

Proceeding in the same manner, the other chroman compounds, made similar to Compound 37, are converted to their respective acetyl analogs.

4,4-Dimethyl-6-carboxy chroman (Compound 5)

A mixture of 1.0 g (4.9 mmol) of 4,4-dimethyl-6-acetyl chroman (Compound 38), 2.0 g (50 mmol) of NaOH, 60 ml of 10% aqueous sodium hypochlorite solution and 18 ml of dioxane was heated at 60° C. with stirring for 3 hours. The reaction mixture was cooled to room temperature and then treated with sodium metabisulphite until the mixture was negative to the potassium iodide/starch test. The reaction mixture was then acidified with conc. HCl and the resultant precipitate was collected by filtration. The residue was washed with water and dried under vacuum to give the title compound as a white solid. PMR (CDCl$_3$): & 1.25 (6H, s), 1.81–1.90 (2H, m), 4.22–4.30 (2H, m), 6.83 (1H, d, J~8.1 Hz), 7.84 (1H, dd, J~8.1 Hz, 1.8 Hz), 8.07 (1H, d, J~1.8 Hz). MS exact mass, m/e 206.0939 (calcd. for C$_{12}$H$_{14}$O$_3$, 206.0943).

In a similar manner, but substituting the corresponding 7-alkyl 4,4-dimethyl-6-acetylchroman derivative for Compound 38, there may be prepared the following compounds:
4,4,7-trimethyl-6-carboxychroman;
4,4-dimethyl-7-ethyl-6-carboxychroman;
4,4-dimethyl-7-propyl-6-carboxychroman; and
4,4-dimethyl-7-pentyl-6-carboxychroman.

Ethyl 4-(4,4-dimethyl-6-chromanolyeoxy) benzoate (Compound 40).

To a solution of 207.5 mg (1.006 mmol) of 4,4-dimethyl-6-carboxychroman (Compound 5) and 168.7 mg (1.015 mmol) of ethyl 4-hydroxybenzoate (Compound 41) in 20 ml of methylene chloride was added 209.5 mg (1.017 mmol) of 1,3-dicyclohexylcarbodiimide and 34 mg (0.278 mmol) of 4-dimethylaminopyridine. The reaction mixture was stirred at room temperature for 24 hours and was then filtered and the residue was washed with 10 ml of methylene chloride. The filtrate was concentrated in-vacuo and the residue was purified by flash chromalography (silica, 6% ethyl acetate in hexanes) to give the title compound as a white solid. PMR (CDCl$_3$): & 1.40–1.46 (9H, m), 1.88–1.93 (2H, m), 4.29–4.34 (2H, m), 4.42 (2H, q, J~7.8 Hz), 6.90 (1H, d, J~9.0 Hz), 7.30 (2H, d, J~9.0 Hz), 7.94 (1H, dd, J~9.0 Hz, 2.3 Hz), 8.12–8.17 (3H, m).

By substituting the compounds 4,4,7-trimethyl-6-carboxychroman; 4,4-dimethyl-7-ethyl-6-carboxychroman; 4,4-dimethyl-7-propyl-6-carboxychroman, and 4,4-dimethyl-7-pentyl-6-carboxychroman for Compound 5 in the above described reaction, the following examples of compounds of the invention can be obtained:
ethyl 4-(4,4,7-trimethyl-6-chromanoyloxy) benzoate;
ethyl 4-(4,4,-dimethyl-7-ethyl-6-chromanoyloxy) benzoate;
ethyl 4-(4,4,-dimethyl-7-propyl-6-chromanoyloxy) benzoate;
ethyl 4-(4,4,-dimethyl-7-pentyl-6-chromanoyloxy) benzoate;

By substituting, for example methyl or propyl 4-hydroxybenzoate for ethyl 4-hydroxybenzoate (Compound 41), the following exemplary compounds of the invention can be obtained.
methyl 4-(4,4,-dimethyl-6-chromanoyloxy) benzoate;
methyl 4-(4,4,7-trimethyl-6-chromanoyloxy) benzoate;
methyl 4-(4,4,-dimethyl-7-ethyl-6-chromanoyloxy) benzoate;
methyl 4-(4,4,-dimethyl-7-propyl-6-chromanoyloxy) benzoate;
methyl 4-(4,4,-dimethyl-7-pentyl-6-chromanoyloxy) benzoate;
propyl 4-(4,4,-dimethyl-6-chromanoyloxy) benzoate;
propyl 4-(4,4,7-trimethyl-6-chromanoyloxy) benzoate;
propyl 4-(4,4,-dimethyl-7-ethyl-6-chromanoyloxy) benzoate;
propyl 4-(4,4,-dimethyl-7-propyl-6-chromanoyloxy) benzoate;
propyl 4-(4,4,-dimethyl-7-pentyl-6-chromanoyloxy) benzoate;

Phenyl 3,3-dimethylacrylate (Compound 42)

To an ice bath cooled solution of 1.29 g (54 mmol) of NaH (obtained from a 60% suspension in mineral oil by 3×10 ml hexane wash) in 20 ml of dry THF was added slowly under oxygen a solution of 5 g (53 mmol) of phenol in 50 ml of dry THF. The mixture was then treated with a solution of 7 g (59 mmol) of dimethylacryloyl chloride in 30 ml of dry THF. The cooling bath was then removed and the mixture was stirred for a further 2.5 h. The reaction mixture was then poured into 150 ml of water containing 1 ml of glacial acetic acid. The mixture was extracted with 150 ml ether and the ether extract washed with saturated NaCl solution and then dried (MgSO$_4$). The solvent was removed in vacuo and the residue purified by flash chromatography (silica; 5% ether in hexanes) to give the title compound as a yellow oil. PMR (CDCl$_3$)): & 1.99 (3H, s), 2.24 (3H, s), 5.93 (1H, broad s), 7.10 (2H, d, J~7.8 Hz) 7.22 (1H, t, J~7.8 Hz), 7.38 (2H, t, J~7.8 Hz).

4,4-Dimethyl-2-oxo-chroman (Compound 43)

To a stirred, ice-cooled suspension of 10.4 g (78 mmol) of aluminum chloride in 160 ml of methylene chloride was added slowly under argon a solution of 7 g (39.8 mmol) of phenyl 3,3-dimethylacrylate (Compound 42) in 40 ml of methylene chloride. The cooling bath was removed and the mixture stirred for a further 42 h. The mixture was poured into a mixture of ice and brine and the organic layer separated. The aqueous layer was extracted with methylene chloride and the organic extracts were combined and washed with saturated NaCl solution and then dried (MgSO$_4$). The solvent was removed in vacuo and the residue purified by flash chromatography (silica; 10% ether in hexane) to give the title compound as a colorless oil. PMR (CDCl$_3$ & 1.30

(6H, s), 2.56 (2H, s), 7.06 (1H, dd, J~8.0 Hz, 1.4 Hz), 7.16 (1H, td, J~8.0 Hz, 1.4 Hz), 7.26 (1H, td, J~8.0 Hz, 1.7 Hz), 7.33 (1H, dd, J~8 0 Hz, 1.7 Hz). MS exact mass, m/e 176.0852 (calcd. for C$_{11}$H$_{12}$O$_2$, 176.0837.)

2-(1,1,3-Trimethyl-3-hydroxybutyl)phenol (Compound 44)

To 11 ml of 3.0 M (33 mmol) methyl magnesium chloride in THF, cooled in an ice bath, was added, under nitrogen, a solution 1.96 g (11.1 mmol) of 4,4-dimethyl-2-oxo-chroman (Compound 43) in 35 ml of dry ether. The cooling bath was then removed and the stirred at room temperature for 72 h. The reaction mixture was then poured onto a mixture of 100 g of ice and 3 ml of conc. H$_2$SO$_4$ and stirred until the magnesium salts were dissolved. The organic layer was separated and the aqueous layer with 2×50 ml of ether. The organic layers were combined and washed successively with water, saturated NaHCO$_3$ and saturated NaCl solutions and then dried (MgSO$_4$). The solvent was removed in vacuo and the residue was purified by flash chromatography (silica; 20% ethyl acetate in hexanes) to give the title compound as a pale yellow solid. PMR (CDCl$_3$): & 1.13 (6H, s), 1.48 (6H, s), 1.89 (1H, s), 2.23 (2H, s), 6.60 (1H, dd, J~7.9 Hz, 1.4 Hz), 6.83 (1H, s), 6.84 (1H, td, J~7.9 Hz, 1.4 Hz), 7.07 (1H, td, J~7.9 Hz, 1.6 Hz), 7.31 (1H, dd, J~7.9 Hz, 1.6 Hz). MS exact mass, m/e 208.1458 (calcd. for C$_{13}$H$_{20}$O$_2$, 208.1464).

2,2,4,4-Tetramethyl-chroman (Compound 45)

A mixture of 2.98 g (14.3 mmol) of 2-(1,1,3-trimethyl-3-hydroxybutyl) phenol (Compound 44) and 40 ml of 20% aqueous H$_2$SO$_4$ was heated at reflux, under nitrogen, for 4 h. The mixture was stirred at room temperature for a further 72 h and then diluted with 50 ml of water. The mixture was extracted with 3×20 ml of hexanes. The organic extracts were then combined and washed successively with water and saturated NaCl solution and then dried (MgSO$_4$). The solvent was then removed in vacuo to give the title compound as a colorless oil. PMR (CDCl$_3$): & 1.36 (6H, s), 1.37 (6H, s), 1.83 (2H, s), 6.71 (1H, dd, J~8.2 Hz, 1.5 Hz), 7.09 (1H, td, J.8.2 Hz, 1.5 Hz) 6.92 (1H, td, J~8.2 Hz, 1.5 Hz), 7.09 (1H, td, J~8.2 Hz, 1.5 Hz), 7.29 (1H, dd, J~8.2 Hz, 1.5 Hz).

2,2,4,4-Tetramethyl-6-acetyl-chroman (Compound 46)

To an ice bath cooled solution of 2 g (10.53 mmol) of 2,2,4,4-tetramethylchroman (Compound 45) in 25 ml of nitromethane was added, under nitrogen, 941 mg (11.99 mmol) of acetyl chloride followed by 1.59 g (11.92 mmol) of aluminum chloride. The cooling bath was then removed and the mixture stirred at room temperature for 16 h. The mixture was then cooled again in an ice bath and treated with 25 ml of conc. HCl. The mixture was then filtered and the residue washed with methylene chloride. The filtrate was concentrated in vacuo and the resultant residue was purified by flash chromatography (silica; 10% ethyl acetate in hexanes) to give the title compound as a yellow oil. PMR (CDCl$_3$) & 1.38 (6H, s), 1.39 (6H, s), 1.87 (2H, s), 2.56 (3H, s), 6.83 (1H, d, J~8.7 Hz), 7.71 (1H, dd, J~8.7 Hz, 2.1 Hz), 7.98 (1H, d, J~2.1 Hz). MS exact mass, m/e 232.1468 (calcd. for C$_{13}$H$_{20}$O$_2$, 232.1464).

2,2,4,4-Tetramethyl-6-carboxychroman. (Compound 47)

A solution of 2.0 (50 mmol) of NaOH in 10 ml of water was treated with 50 ml of 10% aqueous sodium hypochlorite solution and then with a solution of 1.04 g (4.31 mmol) of 2,2,4,4-tetramethyl-6-acetylchroman (Compound 46) in 15 ml of dioxane. The mixture was heated at 65° C. for 40 hours under a nitrogen atmosphere. The mixture was cooled to room temperature and then diluted with water. The mixture was then washed with ether and the aqueous layer was treated with sodium metabisulphite until it was negative to the potassium iodide - starch test. The aqueous layer was then acidified with 10% H$_2$SO$_4$ and then extracted with ether. This ether extract was washed with water and saturated NaCl solution and then dried (MgSO$_4$). Solvent was removed in-vacuo and the residue recrystallized from ethyl acetate to give the title compound as a white solid. PMR (CDCl$_3$): & 1.39 (6H, s), 1.40 (6H, s), 1.88 (2H, s), 6.85 (1H, d, J~8.7 Hz), 7.85 (1H, dd, J~8.7 Hz, 2.1 Hz), 8.09 (1H, d, J~2.1 Hz). MS exact mass, m/e 234.1256 (calcd. for C$_{14}$H$_{18}$O$_3$, 234.1256).

Ethyl 4-(2,2,4,4-tetramethyl-6-chromanoyloxy) benzoate. (Compound 1)

A solution of 200 mg (0.855 mmol) of 2,2,4,4-tetramethyl-6-carboxychroman (Compound 47) and 143.6 mg (0.864 mmol) of ethyl 4-hydroxy-benzoate (Compound 41) in 2 ml of methylene chloride was treated sequentially with 178.5 mg (0.867 mmol) of 1,3-dicyclohexylcarbodiimide and 28.5 mg (0.233 mmol) of 4-dimethylaminopyridine. The mixture was stirred under nitrogen for 17 hours and then filtered. The filtrate was concentrated in-vacuo and the resulting residue was purified by flash chromatography (silica; 10% ethyl acetate in hexanes) to give the title compound as a white solid. PMR (CDCl$_3$): & 1.38–1.44 (15 H, m), 1.90 (2H, s), 4.40 (2H, q, J~7.2 Hz), 6.89 (1H, d, J~8.6 Hz), 7.29 (2H, d, J~8.7 Hz), 7.94 (1H, dd, J~8.6 Hz, 2.2 Hz), 8.11–8.17 (2H, m). MS exact mass, m/e for MH+ 383.1848 (calcd. for C$_{23}$H$_{27}$O$_5$, 383.1859).

Benzyl 4-(2,2,4,4-tetramethyl-6-chromanoyloxy) benzoate (Compound 48)

A solution of 300 mg (1.282 mmol) of 2,2,4,4-tetramethyl-6-carboxychroman (Compound 47) and 293 mg (1.285 mmol) of benzyl 4-hydroxy-benzoate (Compound 49) in 2 ml of methylene chloride was treated sequentially with 264 mg (1.282 mmol) of 1,3-dicyclohexyl-carbodiimide and 38.7 mg (0.317 mmol) of 4-dimethylaminopyridine. The mixture was stirred under nitrogen for 17 hours and then filtered. The residue was purified by flash chromatography (silica; 10% ethyl acetate in hexane) to give the title compound as a pale yellow oil. PMR (CDCl$_3$): & 1.39 (6H, s), 1.41 (6H, s), 1.89 (2H, s), 5.38 (2H, s), 6.89 (1H, d, J~8.4 Hz), 7.29 (2H, d, J~8.7 Hz), 7.34–7.49 (5H, m), 7.94 (1H, dd, J~8.4 Hz, 2.2 Hz), 8.13–8.19 (3H, m). MS exact mass, m/e for MH+ 445.2009 (calcd. for C$_{28}$H$_{29}$O$_5$, 445.2016).

By substituting, for example, methyl or propyl 4-hydroxybenzoate for benzyl 4-hydroxybenzoate or for ethyl 4-hydroxybenzoate as in the immediately preceding two specific examples, methyl 4-(2,2,4,4,-tetramethyl-6-chromanoyloxy) benzoate and propyl 4-(2,2,4,4,-tetramethyl-6-chromanoyloxy) benzoate can be obtained, respectively.

4-(2,2,4,4-Tetramethyl-chromanoyloxy) benzoic acid (Compound 2)

To a solution of 300 mg (0.676 mmol) of benzyl 4-(2,2,4,4-tetramethyl-6-chromanoyloxy) benzoate (Compound 48) in 9 ml of ethyl acetate was added 100 mg of 10% palladum on carbon. The mixture was placed under a hydrogen atmosphere and stirred at room temperature for 3.5 hours. The mixture was then filtered through celite and the filtrate was concentrated in-vacuo to give the title compound as a white solid. PMR (CDCl$_3$): & 1.41 (6H, s), 1.42 (6H, s), 1.91 (2H, s), 6.90 (1H, d, J~8.7 Hz), 7.34 (2H, d, J~8.7 Hz), 7.95 (1H, dd, J~8.7 Hz, 2.1 Hz), 8.17 (1H, d, J~2.1 Hz), 8.21 (2H, d, J~8.7 Hz). MS exact mass, m/e for MH+355.1534 (calcd. for C$_{21}$H$_{23}$O$_5$, 355.1545).

3-Methyl-phenyl-3,3-dimethylacrylate (Compound 50)

A 60% suspension of sodium hydride (3.22 g; 81 mmol) in mineral oil was washed with 3×10 ml of hexane and then treated with 30 of dry THF. This mixture was cooled in an ice-bath and then treated with a solution of 8.6 g (79.5 mmol) of m-cresol in 80 ml of dry THF. The reaction mixture was stirred for 10 min and then treated with a solution of 10.5 g (88.5 mmol) of dimethylacryloyl chloride in 40 ml of dry THF. The reaction mixture was stirred at room temperature for 96 h and then poured into a mixture of 150 ml of water and 1 ml of glacial acetic acid. The mixture was stirred for 10 min and the organic layer was separated. The aqueous layer was extracted with 2×50 ml of ether. The organic layers were combined and washed successively with water and saturated NaCl solution and then dried (M$_g$SO$_4$). The solvent was removed in vacuo and the residue was purified by flash chromatography (silica; 10% ethyl acetate in hexane) to give the title compound as a pale yellow oil. PMR (CDCl$_3$): & 1.95 (3H, d, J~1.3 Hz), 2.21 (3H, d, J~1.2 Hz), 2.34 (3H, s), 5.90 (1H, broad S), 6.86–6.93 (2H, m), 7.01 (1H, d, J~7.2 Hz), 7.24 (1H, t, J~7.2 Hz).

2-(1,1,3-Trimethyl-3-hydroxybutyl) 5-methyl-phenol (Compound 51)

To an ice-bath cooled suspension of 13 g (97.4 mmol) of aluminum chloride in 200 ml of methylene chloride was added dropwise under argon a solution of 9.0 g (47.4 mmol) of 3- methyl-phenyl1,3,3-dimethylacrylate (Compound 50) in 100 ml of methylene chloride. The reaction mixture was stirred at 0 degrees C. for a further 30 in and then at room temperature for 15 h. The reaction mixture was poured into 200 ml of an ice water/salt mixture and the organic layer was separated. The aqueous layer was extracted with 50 ml of ether. The organic layers were combined and washed successively with water and saturated NaCl solution and then dried (MgSO$_4$). The solvent was removed in vacuo and the residue purified by flash chromatography (silica; 5% ethyl acetate in hexane) to give an approximately 2.5:1 mixture of isomeric products, 4,4,7-trimethyl-2-oxo-chroman and 4,4,5-trimethyl-2-oxo-chroman as a pale yellow oil. To a solution of 3.8 g (20 mmol) of this mixture of isomeric 2-oxo-chromans in 60 ml of ether at 0 degrees C. was added under argon 20 ml of 3.0M (60 mmol) of methyl magnesium bromide in ether. The reaction mixture was stirred at room temperature for 48 h and then poured onto a mixture of ice and 1 ml of conc. H$_2$SO$_4$. The organic layer was separated and the aqueous layer extracted with 2×50 ml of ether. The organic layers were combined and washed successively with water, saturated NaHCO$_3$ solution, water again and then saturated NcCl solution and then dried (MgSO$_4$). The solvent was removed in vacuo and the residue was purified by flash chromatography (silica; 15% ethyl acetate in hexanes) to give the title compound as a colorless oil. PMR (CDCl$_3$): & 1.14 (6H, s), 1.45 (6H, s), 2.19 (3H, s), 2.21 (2H, s), 6.39 (1H, d, J~1.8 Hz), 6.67 (1H, dd, J~7.9 Hz, 1.8 Hz), 7.16 (1H, d, J~7.9 Hz), 7.44 (1H, s).

2,2,4,4,7-Pentamethyl-chroman (Compound 52)

To 2.16 g (11.7 mmol) of 2-(1,1,3-trimethyl-3-hydroxybutyl) 5-methyl-phenol (Compound 51) was added under nitrogen 50 ml of 20% aqueous sulfuric acid. The reaction mixture was heated at reflux for 13 h and then cooled. The organic layer was separated and the aqueous layer was extracted with ether. The organic extracts were combined and washed successively with water, saturated NaHCO$_3$ solution, water again and saturated NaCl solution and then dried (MgSO$_4$). The solvent was removed in vacuo to give the title compound as a yellow oil. PMR (CDCl$_3$): & 1.32 (6H, s), 1.34 (6H, s), 1.81 (2H, s), 2.26 (3H, s), 6.63 (1H, s), 6.72 (1H, d, J~7.9 Hz), 7.15 (1H, d, J~7.9 Hz).

2,2,4,4,7-Pentamethyl-6-acetyl-chroman (Compound 53)

To an ice-bath cooled solution of 1.96 g (9.6 mmol) of 2,2,4,4,7-pentamethyl-chroman (Compound 52) in 30 ml of nitromethane was added under argon 1.059 g (13.5 mmol) of acetyl chloride followed by 1.9 g (14.3 mmol) of aluminum chloride. The reaction mixture was stirred at room temperature for 14 h and then cooled in an ice-bath and treated with 25 ml of conc. HCl. The mixture was warmed to room temperature and diluted with ether and water. The organic layer was separated and the aqueous layer extracted with ether. The organic extracts were combined and washed successively with water, saturated NaHCO$_3$ solution, water again, and saturated NaCl solution, and then dried (MgSO₄). The solvent was removed in vacuo and the residue was purified by flash chromatography (silica; 5% ethyl acetate in hexanes) to give the title compound as a pale yellow oil. PMR (CDCl₃): 1.36 (6H, s), 1.37 (6H, s), 1.86 (2H, s), 2.49 (3H, s), 2.56 (3H, s), 6.65 (1H, s), 7.74 (1H, s).

Starting with 3-ethyl, 3-propyl or 3-pentyl phenol instead of meta-cresol, and proceeding through the analogs of the intermediate compounds 50–52, the following examples of analogs of the title compound can be prepared:

2,2,4,4-tetramethyl-7-ethyl-6-acetyl-chroman;
2,2,4,4-tetramethyl-7-propyl-6-acetyl-chroman, and
2,2,4,4-tetramethyl-7-pentyl-6-acetyl-chroman.

2,2,4,4,7-Pentamethyl-6-carboxychroman (Compound 54)

A mixture of 950 mg (3.9 mmol) of 2,2,4,4,7-pentamethyl-6-acetylchroman (Compound 53), 100 ml of 10% sodium hypochlorite solution, 10 ml of a solution of 1.52 g (38 mmol) of sodium hydroxide in water and 10 ml of dioxane was heated at 45° C. for 72 hours. The mixture was cooled to room temperature and washed with 2×25 ml of ether. The aqueous layer was then treated with sodium metabisulphite until it was negative to the potassium iodide-starch test. The aqueous layer was acidified to pH=2 with dilute H₂SO₄ and the mixture was then stored in the refrigerator for 48 hours. The mixture was extracted with 3×25 ml of ether. The ether extracts were then combined and washed successively with water and saturated NaCl solution and then dried (MgSO₄). The solution was then filtered and the filtrate was concentrated in-vacuo to give the title compound as a white solid. PMR (CDCl₃): & 1.34 (12H, s), 1.82 (2H, s), 2.53 (3H, s), 6.64 (1H, s), 8.03 (1H, s).

Starting with the corresponding 7-ethyl, 7- propyl or 7-pentyl analog of 2,2,4,4,7 pentamethyl-6-acetylchroman in the above-described reaction, the following compounds can be obtained:

2,2,4,4-tetramethyl-7-ethyl-6-carboxychroman;
2,2,4,4-tetramethyl-7-propyl-6-carboxychroman, and
2,2,4,4-tetramethyl-7-pentyl-6-carboxychroman.

Ethyl 4-(2.2.4.4.7-pentamethyl-6-chromanoyloxy) benzoate (Compound 3)

A solution of 197.3 mg (0.796 mmol) of 2,2,4,4,7-pentamethyl-6-carboxychroman (Compound 54) and 166.5 mg 1.002 mmol) of ethyl 4-hydroxy benzoate (Compound 41) in 2 ml of methylene chloride was treated under argon with a solution of 165 mg (0.801 mmol) of 1,3-dicyclohexylcarbodiimide and 30 mg (0.246 mmol) of 4-dimethylaminopyridine in 1 ml of methylene chloride. The mixture was stirred at room temperature for 40 hours and then filtered. The filtrate was concentrated in-vacuo and the resultant residue was purified by flash chromatography (silica, 3% ethyl acetate in hexanes) to give the title compound as a white solid. PMR (CDCl₃): & 1.37–1.46 (15 H, m), 1.88 (2H, s), 2.58 (3H, s), 4.39 (2H, q, J~7.2 Hz), 6.73 (1H, s), 7.28 (2H, d, J~8.6 Hz), 8.13 (2H, d, J~8.6 Hz), 8.16 (1H, s). MS exact mass, m/e for MH⁺ 397.2007 (calcd. for C₂₄H₂₉O₅, 397.2014).

By substituting the corresponding 7-ethyl, 7-propyl or 7-pentyl compound for 2,2,4,4,7-pentamethyl-6-carboxychroman, and/or methyl 4-hydroxybenzoate, propyl 4-hydroxybenzoate, or benzyl 4-hydroxybenzoate for ethyl 4-hydroxybenzoate in the above reaction, the following further examples of compounds of the invention can be obtained:

methyl 4-(2,2,4,4,7-pentamethyl-6-chromanoyloxy) benzoate;
propyl 4-(2,2,4,4,7-pentamethyl-6-chromanoyloxy) benzoate;
benzyl 4-(2,2,4,4,7-pentamethyl-6-chromanoyloxy) benzoate [PMR (CDCl₃): & 1.39 (6H, s), 1.40 (6H, s), 1.87 (2H, s), 2.58 (3H, s), 5.38 (2H, s), 6.72 (1H, s), 7.28 (2H, d, J~8.7 Hz), 7.34–7.49 (5H, m), 8.13–8.19 (3H, m).];
methyl 4-(2,2,4,4-tetramethyl-7-ethyl-chromanoyloxy) benzoate;
ethyl 4-(2,2,4,4-tetramethyl-7-ethyl-chromanolyloxy) benzoate
propyl 4-(2,2,4,4-tetramethyl-7-ethyl-6-chromanoyloxy) benzoate;
benzyl 4-(2,2,4,4-tetramethyl-7-ethyl-6-chromanoyloxy) benzoate;
methyl 4-(2,2,4,4-tetramethyl-7-propyl-6-chromanoyloxy) benzoate;
ethyl-4-(2,2,4,4-tetramethyl-7-propyl-6-chromanoyloxy) benzoate;
propyl 4-(2,2,4,4-tetramethyl-7-propyl-6-chromanoyloxy) benzoate;
benzyl 4-(2,2,4,4-tetramethyl-7-propyl-6-chromanoyloxy) benzoate;
methyl 4-(2,2,4,4-tetramethyl-7-pentyl-6-chromanoyloxy) benzoate;
ethyl 4-(2,2,4,4-tetramethyl-7-pentyl-6-chromanoyloxy benzoate;
propyl 4-(2,2,4,4-tetramethyl-7-pentyl-6-chromanoyloxy benzoate;
benzyl 4-(2,2,4,4-tetramethyl-7-pentyl-6-chromanoyloxy benzoate;

By removing the benzyl group from the corresponding benzyl esters shown above (in analogy to the synthesis of Compound 2 by hydrogenation of benzyl 4-(2,2,4,4-tetramethyl-6-chromanoyloxy) benzoate, Compound 48), the following free carboxylic acids can be obtained:

4-(2,2,4,4,7-pentamethyl-6-chromanoyloxy) benzoic acid (Compound 4) [PMR (CDCl₃) : & 1.40 (6H, s), 1.42 (6H, s), 1.89 (2H, s), 2.60 (3H, s), 6.74 (1H, s), 7.34 (2H, d, J~8.6 Hz), 8.18 (1H, s), 8.22 (2H, d, J~8.6 Hz)];
4-(2,2,4,4-tetramethyl-7-ethyl-chromanoyloxy) benzoic acid;
4-(2,2,4,4-tetramethyl-7-propyl-6-chromanoyloxy) benzoic acid;
4-(2,2,4,4-tetramethyl-7-pentyl-6-chromanoyloxy) benzoic acid.

4-(2-Hydroxyphenyl)-2-methyl-2-butanol (Compound 55)

To an ice-cooled solution of methyl magnesium bromide in ether (104 ml × 2.7M; 0.28 mole) was added slowly, under nitrogen, a solution of 13.8 g (0.093 mole) of dihydrocoumarin (Compound 28, Scheme 8) in 230 ml of dry ether. The cooling bath was then removed and the mixture stirred for a further 16 hours. The reaction mixture was then poured onto 300 g of ice and 10 ml of conc. H₂SO₄ and the mixture was stirred to ensure dissolution. The organic layer was then separated and the aqueous layer was extracted with 2×100 ml of ether. The organic layers were combined and washed successively with 70 ml portions of water, saturated NaHCO₃, 2M Na₂S₂O₃ and saturated NaCl and then dried (Na$_2$SO$_4$). The solution was then filtered and the filtrate concentrated in-vacuo to give the title compound as a white solid. PMR (CDCl$_3$) : & 1.30 (6H, s), 1.80 (2H, t, J~7.5 Hz), 2.12 (1H, broad s), 2.73 (2H, t, J~7.5 Hz), 6.80–6.87 (2H, m), 7.00 (1H, broad s), 7.07–7.14 (2H, m).

2,2-Dimethylchroman (Compound 56).

A mixture of 16 g (89 mmol) of 4-(2-hydroxyphenyl)-2-methyl-2-butanol, (Compound 55), 40 ml of conc. H$_2$SO$_4$ and 160 ml of water was heated at reflux for 4 hours. The mixture was cooled, diluted with 300 ml of water and extracted with 2×100 ml of hexane. The organic extracts were combined, washed successively with water and saturated NaCl solution and then dried. The solution was then filtered and the filtrate concentrated in-vacuo to give the title compound as a yellow oil. PMR (CDCl$_3$) : & 1.32 (6H, s), 1.78 (2H, t, J~6.8 Hz), 2.76 (2H, t, J~6.8 Hz), 6.74–6.85 (2H, m), 7.01–7.12 (2H, m).

2,2-Dimethyl-6- acetylchroman (Compound 57)

A solution of 5.0 g (30.82 mmol) of 2,2-dimethylchroman (Compound 56) in 50 ml of nitromethane was treated, under nitrogen, with 2.53 g (32.35 mmol) of acetyl chloride followed by 4.4 g (33 mmol) of aluminum chloride. The reaction mixture was stirred at room temperature for 3 hours and then cooled in an ice-bath and treated slowly with 50 ml of 6M HCl. The mixture was diluted with water and extracted with ether. The ether extracts were washed successively with saturated NaHCO$_3$ solution, water and saturated NaCl solution and then dried (MgSO$_4$). The solvent was removed in-vacuo and the resultant residue was purified by flash chromatography (silica; 10% ethyl acetate in hexane) to give the title compound as a white solid. PMR (CDCl$_3$) : & 1.36 (6H, s), 1.84 (2H, t, J~6.8 Hz), 2.54 (3H, s), 2.82 (2H, t, J~6.8 Hz), 6.80 (1H, d, J~8.4 Hz), 7.69–7.76 (2H, m). MS exact mass, m/e 204.1140 (calcd. for C$_{13}$H$_{16}$O$_2$, 204.1150).

2,2-Dimethyl-6-carboxychroman (Compound 58)

A mixture of 5.8 g (28.4 mmol) of 2,2-dimethyl-6-acetylchroman (Compound 57), 75 ml of dioxane, 300 ml of 10% sodium hypochlorite solution and 50 ml of a 20% solution of NaOH in water was heated at 65° C. for 0.5 hour. The mixture was then treated with another 200 ml of 10% sodium hypochlorite solution and then heated at 65° C. for a further 65 hours. The mixture was cooled to room temperature and washed with ether. The aqueous layer was then treated with sodium metabisulphite solution until it was negative to the potassium iodide-starch test. The aqueous solution was then acidified to pH=4 with dilute H$_2$SO$_4$ and stored in the refrigerator for 48 hours. The solution was then diluted with water and extracted with ether. The ether layers were combined and washed with saturated NaCl solution and then dried (MgSO$_4$). The solution was filtered and the solvent was removed in-vacuo to give the title compound as a white solid. PMR (CDCl$_3$): & 1.36 (6H, s), 1.84 (2H, t, J~6.8 Hz), 6.81 (1H, d, J~8.4 Hz), 7.82–7.89 (2H, m). MS exact mass, m/e 206.0942 (calcd. for C$_{12}$H$_{14}$O$_3$ 206.0943).

Ethyl 4-(2,2-dimethyl-6-chromanoyloxy) benzoate (Compound 59)

To a solution of 206 mg (1.0 mmol) of 2,2-dimethyl-6-carboxychroman (Compound 58) and 173.5 mg (1.04 mmol) of ethyl 4-hydroxy-benzoate (Compound 41) in 2 ml of methylene chloride was added a solution of 206 m9 (1.0 mmol) of 1,3-dicyclohexylcarbodiimide and 31.7 (0.26 mmol) of 4-dimethylaminopyridine. The mixture was stirred at room temperature for 260 hours and then filtered. The residue was washed with methylene chloride and the filtrate was concentrated in-vacuo. The resultant crude product was purified by flash chromatography (silica; 10% ethyl acetate in hexane) to give the title compound as a white solid. PMR (CDCl$_3$) : & 1.36–1.47 (9H, m), 1.86 (2H, t, J~6.7 Hz), 4.39 (2H, q, J~7.3 Hz), 6.86 (1H, d, J~8.4 Hz), 7.27 (2H, d, J~8.7 Hz), 7.91–7.98 (2H, m), 8.12 (2H, d, J~8.7 Hz). MS exact mass, m/e 354.1467 (calcd. for C$_{21}$H$_{22}$O$_5$, 354.1467).

By substituting methyl 4-hydroxybenzoate, propyl 4-hydroxybenzoate or benzyl 4-hydroxybenzoate for ethyl 4-hydroxybenzoate (Compound 41) in the above reaction the following analogs, further examples of compounds of the invention, can be obtained:

methyl 4-(2,2-dimethyl-6-chromanoyloxy) benzoate;

propyl 4-(2,2-dimethyl-6-chromanoyloxy) benzoate, and benzyl 4-(2,2-dimethyl-6-chromanoyloxy) benzoate.

By removing the benzyl group from benzyl 4-(2,2-dimethyl-6-chromanoyloxy) benzoate with hydrogenation, 4-(2,2-dimethyl-6-chromanoyloxy) benzoic acid can be obtained.

4,4-Dimethyl-6-(N,N-diethylcarboxamido) chroman (Compound 60)

A solution of 8.0 g (38.6 mmol) of 4,4-dimethyl-6-carboxy-chroman (Compound 5) in 8.5 ml (13.86 g, 116.5 mmol) of thionyl chloride was heated at reflux for 1 hour under argon in an apparatus filled with a drying tube and HCl trap. The reaction mixture was cooled to room temperature and the excess thionyl chloride was removed under vacuum using a cryogenic trap. The resultant crude acid chloride was dissolved in 8 ml of toluene and transferred via syringe to a solution of 8.52 g (116.5 mmol) of diethylamine in 10 ml of toluene at 0° C. under an argon atmosphere. The cooling bath was removed and the reaction mixture was stirred at room temperature for 22 hours. The reaction mixture was then treated with 50 ml of water, stirred for 5 min and the organic layer was then separated. The aqueous layer was extracted with 15 ml of ether and the organic extracts were combined and washed with saturated NaCl solution and then dried (MgSO$_4$). The solution was filtered and the solvent was removed in-vacuo to give the title compound as pale brown crystals. PMR (CDCl$_3$) & 1.05–1.20 (6H, broad s), 1.28 (6H, s), 1.72–1.81 (2H, m), 3.15–3.52 (4H, broad s), 4.10–4.18 (2H, m), 6.70 (1H, d, J~8.1 Hz), 7.04 (1H, d, J~8.1 Hz, 1.8 Hz), 7.26 (1H, d, J~1.8 Hz).

4,4,7-Trimethyl-6-(N,N-diethylcarboxamido) chroman (Compound 6i)

To a stirred solution of 489.7 mg (4.21 mmol) of tetramethyl ethylenediamine, 3.24 ml of 1.3 M (4.21 mmol) sec-butyl lithium in hexane and 4.7 ml of dry THF at −78° C. was added dropwise under argon, a solution of 1 g (3.83 mmol) of 4,4-dimethyl-6-(N,N-diethylcarboxamido) chroman (Compound 60) in 14.7 ml of dry THF. The reaction mixture was stirred at −78° C. for a further 1 hour and then treated with 1.36 g (9.58 mmol) of methyl iodide. The cooling bath was then removed and the reaction mixture was stirred at room temperature for 2 hours. The reaction mixture was treated with 3 ml of water and the THF was removed in-vacuo. The residue was extracted with ether and the combined ether extracts were washed successively with 10 ml of saturated NaHCO$_3$ solution, 10 ml of dilute HCl and 20 ml of saturated NaCl solution and then dried (MgSO$_4$). The solvent was removed in-vacuo and the residue was purified by flash chromatography (silica; 10 percent ethyl acetate and 0.5 percent glacial acetic acid in hexane) to give the title compound as a pale yellow oil. PMR (CDCl$_3$): & 1.03 (3H, t, J~7.0 Hz), 1.25 (3H, t, J~7.2 Hz), 1.30 (6H, s), 1.78–1.85 (2H, m), 2.18 (3H, s), 3.12 (2H, q, J~7.0 Hz), 3.35–3.65 (2H, broad s), 4.14–4.21 (2H, m), 6.61 (1H, s), 7.05 (1H, s).

Further examples of the compounds of the invention can be synthesized in accordance with the foregoing procedures or by such modifications thereof which will be readily apparent to the practicing chemist in light of the foregoing disclosure. Examples of Formulation for Topical Administration Preferably the compounds of the invention may be administered topically using various formulations. Such formulations may be as follows:

| Ingredient | Weight/Percent |
| --- | --- |
| Solution | |
| Retinoid (active ingredient) | 0.1 |
| BHT | 0.1 |
| Alcohol USP | 58.0 |
| Polyesthylene Glycol 400 NF | 41.8 |
| Gel | |
| Retinoid (active ingredient) | 0.1 |
| BHT | 0.1 |
| Alcohol USP | 97.8 |
| Hydroxypropyl Cellulose | 2.0 |

What is claimed is:

1. A compound of the formula

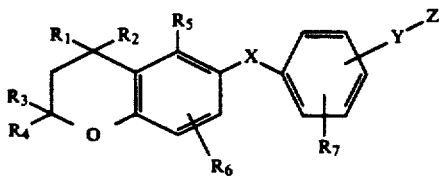

wherein
the R$_1$-R$_7$ groups are independently H or straight chain lower alkyl group of 1 to 6 carbons or branched chain lower alkyl or cycloalkyl groups of 3 to 6 carbons;
X is —COO—;
Y is cycloalkyl or branched chain alkyl group of 3 to 6 carbons, or is (CH$_2$)$_n$ where n is an integer between 0 to 6, and
Z is H, OH, OR', OCOR', —COOH or a pharmaceutically acceptable salt, ester or amide thereof, —CH$_2$OH —CH$_2$OR', CH$_2$OCOR', or —CHO CH(OR$_8$)$_2$, CHOR$_9$O, or —COR' or CR'(OR$_8$)$_2$, or CR'OR$_9$O where R' is an alkyl group containing 1 to 6 carbons, cycloalkyl group containing 3 to 6 carbons, or alkenyl group containing 2 to 6 carbons, or a phenylalkyl, or phenyl group and where R$_8$ is lower alkyl, and R$_9$ is a divalent alkyl radical of 2 to 5 carbons.

2. A compound of claim 1 where Y is (CH$_2$)$_n$ and n is zero.

3. A compound of claim 2 where Z is COOR* wherein R* is lower alkyl.

4. A compound of claim 2 wherein R$_1$ and R$_2$ are methyl, R$_3$ R$_4$ and R$_5$ are hydrogen.

5. A compound of claim 4 wherein R$_6$ is attached to the 7-position of the chroman nucleus.

6. A compound of claim 2 wherein R$_3$ and R$_4$ are methyl, R$_1$ R$_2$ and R$_5$ are hydrogen.

7. A compound of claim 6 wherein R$_6$ is attached to the 7-position of the chroman nucleus.

8. A compound of claim 2 wherein R$_1$, R$_2$, R$_3$, and R$_4$ are methyl.

9. A compound of claim 8 wherein R$_6$ is attached to the 7-position of the chroman nucleus.

10. One or more compounds set forth in claim 1, comprised in and admixed with a pharmaceutical composition including a pharmaceutically acceptable excipient.

11. A compound of the formula

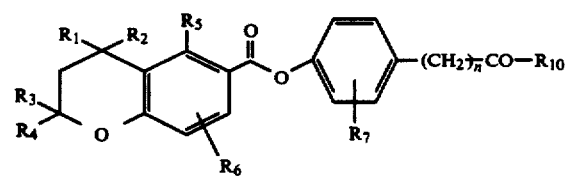

wherein
the R$_1$-R$_7$ groups are independently H or straight chain alkyl group of 1 to 6 carbons or branched chain lower alkyl or cycloalkyl groups of 3 to 6 carbons;
n is an integer between 0 to 6, and R$_{10}$ is OR* where R* is H, lower alkyl, or R$_{10}$ is N(R)$_2$ where R independently is H or lower alkyl, phenyl or lower alkyl phenyl.

12. A compound of claim 11 wherein n is zero.

13. A compound of claim 11 wherein R$_1$-R$_4$ groups are independently H or CH$_3$.

14. One or more compounds set forth in claim 11, comprised in and admixed with a pharmaceutical composition including a pharmaceutically acceptable excipient.

15. A compound of the formula

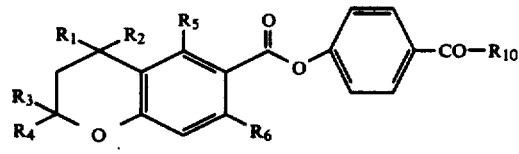

wherein
the R$_1$-R$_4$ groups are independently H or CH$_3$, the R$_5$-R$_6$ groups are independently H or lower alkyl of 1-6 carbons, and R$_{10}$ is OR* where R* is H, lower alkyl, or R$_{10}$ is N(R)$_2$ where R independently is H or lower alkyl.

16. A compound of claim 15 wherein R$_1$ and R$_2$ both are CH$_3$, and R$_3$ and R$_4$ both are H.

17. A compound of claim 16 wherein R$_6$ is H and R* is H or lower alkyl.

18. A compound of claim 15 wherein R$_1$ and R$_2$ both are H, and R$_3$ and R$_4$ are CH$_3$.

19. A compound of claim 18 wherein R$_6$ is H and R* is H or lower alkyl.

20. A compound of claim 15 wherein $R_1$-$R_4$ all are methyl.

21. A compound of claim 20 wherein $R_5$ is H, $R_6$ is H or methyl and R* is H or lower alkyl, or pharmaceutically acceptable salt of the compound where R* is H.

22. A compound of claim 21 wherein $R_6$ is H.

23. The compound of claim 22 wherein R* is ethyl.

24. The compound of claim 22 wherein R* is hydrogen, or pharmaceutically acceptable salt thereof.

25. A compound of claim 21 wherein $R_6$ is methyl.

26. The compound of claim 25 wherein R* is ethyl.

27. The compound of claim 25 wherein R* is hydrogen or pharmaceutically acceptable salt thereof.

28. One or more compounds set forth in claim 15, comprised in and admixed with a pharmaceutical composition including a pharmaceutically acceptable excipient.

* * * * *

UNITED STATES PATENT AND TRADEMARK OFFICE
CERTIFICATE OF CORRECTION

PATENT NO. : 5,006,550
DATED : April 9, 1991
INVENTOR(S) : Roshantha A. S. Chandraratna It is certified that error appears in the above-identified patent and that said Letters Patent is hereby corrected as shown below:

Title Page:
In the abstract, after the formula line 5, "$(CH_2)$" should be —$(CH_2)_n$—;
Column 1, line 28, before "5,6,7,8" insert — - —;
Column 1, line 58, before "a" add —or—;
Column 2, lines 44, "Conversion" should be —conversion of —;
Column 3, line 52, after "Particularly" add —preferred—;
Column 4, line 12, after "alkylating" add —agent—;
Column 4, line 55, "Chromanoyloxly" should be —chromanoyloxy—;
Column 6, line 24, after "followed" delete "is";
Column 8, line 38, "terephathalic" should be —terephthalic—;
Column 8, line 45, "terephathalic" should be —terephthalic—;
Column 8, line 54, "terephtalic" should be —terephthalic—;
Column 9, line 61, "dehyde" should be —aldehyde—;
Column 11, line 55, after "11" add —)—;
Column 12, compound 16 in REACTION SCHEME 7, add —O— to the to of "||";
Column 13, line 57, "R⑧action" should be —Reaction—;
Column 14, line 44, "Grigna" should be —Grignard—;
Column 14, line 55, "20and" should be —20 and—;
Column 15, line 49, "30and" should be —30 and—;
Column 19, line 29, "8 0" should be —8.0—;
Column 19, line 43, before "with" add —extracted—;
Column 20, line 1, delete "8.2 Hz, 1.5 Hz), 7.09 (1H, td, J.8.2";
Column 20, line 20, after "($CDCl_3$)" insert —:—;

UNITED STATES PATENT AND TRADEMARK OFFICE
CERTIFICATE OF CORRECTION

PATENT NO. : 5,006,550
DATED : April 9, 1991
INVENTOR(S) : Roshantha A.S. Chandrearatna It is certified that error appears in the above-identified patent and that said Letters Patent is hereby corrected as shown below:

Column 22, line 4, "97.4" should be —97.5—;

Column 22, line 7, "pehnyl1-3" should be —phenyl-3—;

Column 22, line 10, "30 in" should be —30 min—;

column 23, line 44, "2.2.4.4.7" should be —2,2,4,4,7—;

Column 25, line 61, after "1.84 (2H, t, J~6.8 Hz)" should be —2.83 (2H, t, J~6.8 Hz)—;

Column 25, line 63, "$C_{12}H14o_3$" should be —$C_{12}H_{14}O_3$—;

Column 26, line 3, "m9" should be —mg—;

Column 26, line 4, after "3.17" insert —mg—;

Column 26, line 11, before "4.39" insert —2.86 (2H, t, J~6.7 Hz)—;

Column 26, line 58, "6i" should be —61—;

Column 27, line 19-20, "Examples of Formulation for Topical Administration" should be a heading;

Column 28, line 66, after "$R_4$" add —both—.

Signed and Sealed this

Seventeenth Day of May, 1994

BRUCE LEHMAN

Attest:

*Attesting Officer*       *Commissioner of Patents and Trademarks*

UNITED STATES PATENT AND TRADEMARK OFFICE
CERTIFICATE OF CORRECTION

PATENT NO. : 5,006,550
DATED : April 9, 1991
INVENTOR(S) : Roshantha A.S. Chandraratna It is certified that error appears in the above-identified patent and that said Letters Patent is hereby corrected as shown below:

Column 1, line 18, "0133795" should be —0130795—;

Column 12, line 3, "5))" should be —5)—;

Column 19, line 25, "($CDCl_3$" should be —($CDCl_3$):—;

column 22, line 31, "NcCl" should be —NaCl—.

Signed and Sealed this

Twenty-seventh Day of September, 1994

Attest:

BRUCE LEHMAN

Attesting Officer

*Commissioner of Patents and Trademarks*